US00PP31680P2

(12) United States Plant Patent
Jones

(10) Patent No.: US PP31,680 P2
(45) Date of Patent: Apr. 14, 2020

(54) ***SALVIA* 'SSLVI08-0'**

(50) Latin Name: *Salvia nemorosa*
Varietal Denomination: SSLVI08-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/501,572

(22) Filed: Apr. 30, 2019

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Annette H Para
(74) *Attorney, Agent, or Firm* — Cassandra Bright

(57) ABSTRACT

A new and distinct *Salvia* cultivar named 'SSLVI08-0' is disclosed, characterized by a very compact plant form, early flowering and abundant violet colored flowers. Plants are observed resistant to bacterial leaf spot. The new variety is a *Salvia nemorosa*, normally produced as an outdoor garden or container plant.

1 Drawing Sheet

Latin name of the genus and species: *Salvia nemorosa*.
Variety denomination: 'SSLVI08-0'.

BACKGROUND OF THE INVENTION

The new *Salvia* is a product of a planned breeding program conducted by the inventor, Steve Jones. The new variety originated from a cross-pollination of an unnamed, unpatented proprietary variety of *Salvia nemorosa* with another an unnamed, unpatented proprietary variety of *Salvia nemorosa*. The crossing was made in August 2017 at a commercial greenhouse in Santa Paula, Calif.

The new variety was identified as a potentially interesting selection in November 2017, at a greenhouse in Santa Paula, Calif.

Asexual reproduction of the new cultivar 'SSLVI08-0' by terminal vegetative cuttings was first performed in February 2018, at a research greenhouse in Santa Paula, Calif. Subsequent propagation has shown that the unique features of this cultivar are stable and reproduced true to type on successive generations.

SUMMARY OF THE INVENTION

The cultivar 'SSLVI08-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SSLVI08-0' These characteristics in combination distinguish 'SSLVI08-0' as a new and distinct *Salvia* cultivar:

1. Violet flower color.
2. Very compact plant form.
3. Abundant flowering.
4. Early flowering.
5. Resistance to bacterial leaf spot.

PARENT COMPARISON

Plants of the new cultivar 'SSLVI08-0' are similar to plants of the seed parent in most horticultural characteristics, however, plants of the new cultivar 'SSLVI08-0' differ in the following:

1. The new variety is a more compact plant than the seed parent.
2. The new variety has a longer raceme than the seed parent.
3. The new variety has more branching than the parent.

Plants of the new cultivar 'SSLVI08-0' are similar to plants of the pollen parent in most horticultural characteristics, however, plants of the new cultivar 'SSLVI08-0' differ in the following:

1. The new variety has violet flowers, compared to white flowers of the pollen parent.
2. The new variety begins flowering earlier than the pollen parent.

COMMERCIAL COMPARISON

Plants of the new cultivar 'SSLVI08-0' can also be compared to the commercial variety *Salvia* 'Sensation Violet', unpatented. These varieties are similar in most horticultural characteristics; however 'SSLVI08-0' differs in the following:

1. The new variety is more compact and has more branches than this comparator.
2. The new variety has more flowers per stem than this comparator.
3. The new variety has greater heat resistance than this comparator.
4. The new variety is more disease resistant (bacterial leaf spot) than this comparator.

BRIEF DESCRIPTION OF THE PHOTOGRAPH

The accompanying photograph illustrates in full color a typical plant of 'SSLVI08-0' grown in a greenhouse, in Santa Paula, Calif., in a commercial 35 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SSLVI08-0' plants grown in a greenhouse in Santa Paula, Calif. The growing temperature ranged from approximately 10° C. to 30° C. The greenhouse is un-shaded, giving bright, normal sunlight conditions. Measurements and numerical values represent averages of typical plant types.

Botanical classification: *Salvia nemorosa* 'SSLVI08-0' Swifty Violet Multiflora.

PROPAGATION

Root description: Fine, densely fibrous. Colors include RHS Yellow-White 158D and Orange-White 159C. Grey-Brown 199A and 199B for older roots.

PLANT

Growth habit: Upright and mounding. Compact.

Pot size of plant described: 40 cm diameter pot.

Height: Approximately 17 cm to top of foliage. Approximately 30 cm to top of flowering plane. Measured from soil level of pot.

Plant spread: Approximately 50 cm.

Growth rate: Moderate.

Branching characteristics: Well branched. Average 4 branches emerging from a pinch, which branch into another 4 primary lateral branches.

Length of primary lateral branches: Approximately 5 cm, then forming more branches.

Diameter of lateral branches: Approximately 0.4 cm.

Quantity of lateral branches: About 36 to 48.

Stem:

*Color*.—Near RHS Green 137B. Nodes lightly flushed Violet 83A.

*Texture*.—Pubescent and ribbed.

Internode length: Average range 1.0 cm.

Age of plant described: Approximately 25 weeks from 5 rooted cuttings.

FOLIAGE

Leaf:

*Arrangement*.—Opposite.

*Quantity*.—Average range 6 to 8 fully expanded per main branch.

*Average length*.—Average range 4.5 to 8.0 cm. including petiole.

*Average width*.—Approximately 2.2 cm.

*Shape of blade*.—Narrow deltoid.

*Apex*.—Acute.

*Base*.—Truncate to cordate.

*Attachment*.—Stalked.

*Margin*.—Dentate.

*Texture of top surface*.—Matte, glabrous. Shallow reticulate.

*Texture of bottom surface*.—Matte, glabrous, reticulate.

*Color*.—Young foliage upper side: Near RHS Green 137B. Young foliage under side: Near RHS Green 138B. Mature foliage upper side: Near RHS Green 137B. Mature foliage under side: Near RHS Green 137C.

*Venation*.—Type: Reticulate. Venation color upper side: Near RHS Yellow-Green 144B. Venation color under side: Near RHS Yellow-Green 144B.

*Petiole*.—Average Length: Average range 1.0 to 2.5 cm. Diameter: Approximately 0.2 cm. Color: Near RHS Yellow-Green 144B.

FLOWER

Natural flowering season: Flowering from early Spring through late Summer.

Inflorescence type and habit: Flowers arranged in verticillasters on spikes.

Flower longevity on plant: Individual flowers last approximately 7 to 10 days on the plant. Each spike lasts approximately 4 to 6 weeks with flowers. Corolla self-cleaning, calyx persistent.

Quantity of flowers: About 24 to 36 fully flowers per spike. Mature plants have approximately 30 to 50 spikes.

Spike size:

*Diameter*.—Approximately 2.0 cm.

*Height*.—Approximately 10.0 cm.

Individual flowers:

Size:

*Diameter*.—Approximately 0.7 cm.

*Length*.—Approximately 1.1 cm.

Fragrance: Moderately strong musty scent.

Corolla:

*Petal arrangement*.—The corolla is sympetalous and typically bilabiate with 2 small, fully fused lobes forming a single upper lip and 3 larger fused lobes forming a lower lip.

*Margin*.—Entire.

*Tip shape*.—Upper lip tip obtuse, lower lip tip retuse.

*Length*.—Upper lip Approximately 0.8 cm. Lower lip Approximately 0.6 cm. Tube length Approximately 0.3 cm.

*Width*.—Upper lip: Approximately 0.6 cm, lower lip approximately 0.9 cm. Tube width: Approximately 0.6 cm.

*Texture*.—Upper lip: Glabrous all surfaces. Lower lip: Glabrous all surfaces.

Color:

*Upper lip*.—When opening: Inner surface: Near RHS Violet N88A. Outer surface: Near RHS Violet N88B. Fully opened: Inner surface: Near RHS Violet-Blue N89A. Outer surface: Near RHS Violet-Blue N89B. Fading: Inner surface: Near RHS Violet-Blue N89A. Outer surface: Near RHS Violet-Blue 93B.

Color:

*Lower lip*.—When opening: Inner surface: Near RHS Violet N88A. Outer surface: Near RHS Violet N88B. Fully opened: Inner surface: Near RHS Violet-Blue N89A. Outer surface: Near RHS Violet-Blue N89B. Fading: Inner surface: Near RHS Violet-Blue N89A. Outer surface: Near RHS Violet-Blue 93B.

Color:

*Tube*.—When opening: Inner surface: Near RHS Violet 84C. Outer surface: Near RHS Violet N87D. Fully opened: Inner surface: Near RHS Violet 84C. Outer surface: Near RHS Violet N87D. Fading: Inner surface: Near RHS Violet 84D. Outer surface: Near RHS Violet N87D.

Bud: Flower bud includes immature calyx which completely surrounds immature corolla.

*Shape*.—Ovoid.

*Length*.—Approximately 0.5 cm.

*Diameter*.—Approximately 0.4 cm.

*Color*.—Near RHS Violet N88B.

Calyx:

*Length*.—Approximately 0.5 cm.

*Diameter*.—Approximately 0.3 cm.

*Shape*.—Tubular.

Sepals:

*Shape*.—Quantity per flower: 3, fused to form a tube. Unfused apex.

*Length*.—Approximately 0.2 cm unfused portion.
*Width*.—Approximately 0.2 cm.
*Margin*.—Entire.
*Apex*.—Acute.
*Texture*.—Softly pubescent.
*Color*.—Immature: Near RHS Green 137C flushed Violet N87C. Mature: Near RHS Green 137C, lightly flushed Violet-Blue N89C.

Peduncle:
*Length*.—Average range 2 to 4.0 cm.
*Diameter*.—0.3 cm.
*Color*.—Near RHS Green 138B.
*Orientation*.—Straight, approximately 15 degree angle from center of plant.
*Strength*.—Strong.
*Texture*.—Softly pubescent, ridged.

Pedicels:
*Length*.—Average 0.1 cm.
*Diameter*.—0.1 cm
*Color*.—Near RHS Green 138C.
*Orientation*.—Straight, approximately 45 degree angle from attachment.
*Strength*.—Flexible.
*Texture*.—Pubescent.

REPRODUCTIVE ORGANS

Stamens:
*Number*.—2.
*Filament length*.—Approximately 0.7 cm.
*Filament color*.—Near RHS White N155A.

Anthers:
*Shape*.—Linear.
*Length*.—0.2 cm.
*Color*.—Near RHS Violet-Blue 90C.
*Pollen*.—Scant pollen observed, colored near RHS White N155A.

Pistil:
*Number*.—1.
*Length*.—Approximately 1.0 cm.
*Style*.—Length: Approximately 0.7 cm. Color: Near RHS White N155C.
*Stigma*.—Shape: Forked. Color: Near RHS Violet-Blue 90B. Ovary: Colored near RHS White N155C, oblong, approximately 0. 2 cm long and 0.2 in diameter.

OTHER CHARACTERISTICS

Seeds and fruits: 2 small seeds, round, about 1.5 mm in diameter colored near RHS Brown 200A.

Disease/pest resistance: Observed resistance to bacterial leaf spot. Neither resistance nor susceptibility to other pathogens and pests common to *Salvia nemorosa* have been observed.

Temperature tolerance: The new variety tolerates temperatures within USDA zones 3 to 9.

What is claimed is:

1. A new and distinct cultivar of *Salvia* plant named 'SSLVI08-0' as herein illustrated and described.

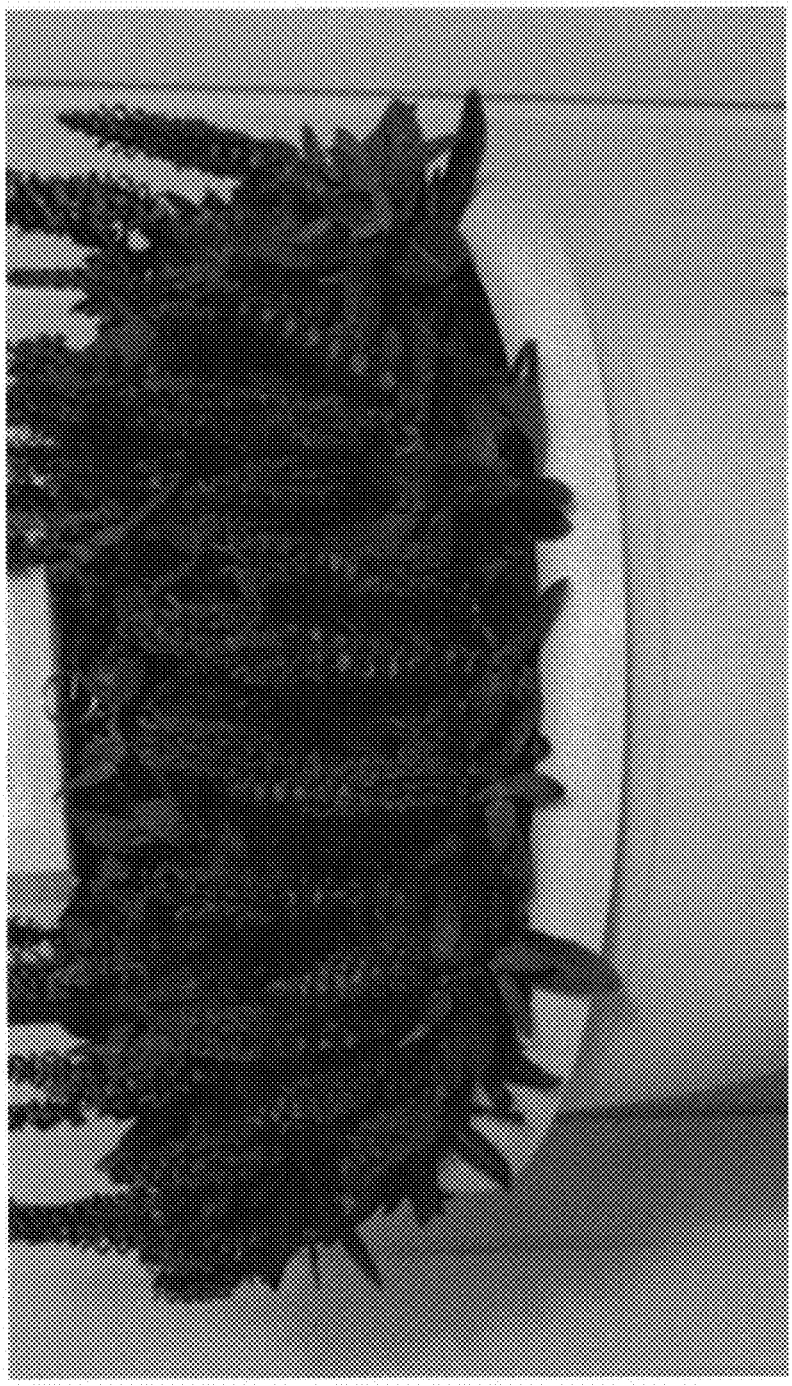

* * * * *